United States Patent
Cheng

(10) Patent No.: US 9,782,525 B2
(45) Date of Patent: Oct. 10, 2017

(54) MULTI-WAY VALVE FOR A MEDICAL INSTRUMENT

(71) Applicant: Gyrus ACMI, Inc., Southborough, MA (US)

(72) Inventor: Ming J. Cheng, W. Warwick, RI (US)

(73) Assignee: GYRUS ACMI, INC., Southborough, MA (US)

( * ) Notice: Subject to any disclaimer, the term of this patent is extended or adjusted under 35 U.S.C. 154(b) by 141 days.

(21) Appl. No.: 14/592,397

(22) Filed: Jan. 8, 2015

(65) Prior Publication Data

US 2016/0199548 A1 Jul. 14, 2016

(51) Int. Cl.
*A61M 1/00* (2006.01)
*A61M 39/22* (2006.01)

(52) U.S. Cl.
CPC ........ *A61M 1/0064* (2013.01); *A61M 1/0062* (2013.01); *A61M 39/223* (2013.01)

(58) Field of Classification Search
CPC ........ A61M 39/223; A61M 2039/2453; A61M 2039/2446; A61M 2039/2466; A61M 1/0058; A61M 1/0062; A61M 1/0064; A61M 2039/246
See application file for complete search history.

(56) References Cited

U.S. PATENT DOCUMENTS

| 4,141,379 A | * | 2/1979 | Manske | ................ A61M 39/24 137/496 |
| 4,254,762 A | | 3/1981 | Yoon | |
| 4,281,646 A | | 8/1981 | Kinoshita | |
| 4,312,375 A | | 1/1982 | Leinemann | |
| 4,354,492 A | * | 10/1982 | McPhee | ................ A61M 5/40 137/528 |
| 4,548,197 A | | 10/1985 | Kinoshita | |
| 4,646,722 A | | 3/1987 | Silverstein et al. | |

(Continued)

FOREIGN PATENT DOCUMENTS

EP 0374727 A1 6/1990
JP H05/038323 A 2/1993
(Continued)

OTHER PUBLICATIONS

US 5,772,579, 06/1998, Reisdorf (withdrawn)
(Continued)

*Primary Examiner* — Emily Schmidt
*Assistant Examiner* — Lauren M Peng
(74) *Attorney, Agent, or Firm* — The Dobrusin Law Firm, P.C.

(57) ABSTRACT

A medical device is provided comprising a first port; a second port in fluid communication with the first port; and a third port in selective fluid communication with both the first port and the second port; a sealing membrane disposed between the third port and both the first port and the second port, the sealing membrane is configured to move between a first position preventing fluid communication between the third port and both the first port and the second port and a second position allowing fluid communication between the third port and the first port, wherein movement of a fluid supplied to the medical device at the third port moves the sealing membrane from the first position to the second position.

7 Claims, 4 Drawing Sheets

(56) References Cited

U.S. PATENT DOCUMENTS

| | | | |
|---|---|---|---|
| 4,762,149 A * | 8/1988 | Pickl, Jr. | F16K 15/148 137/843 |
| 5,170,774 A | 12/1992 | Heckele | |
| 5,176,645 A | 1/1993 | Guerrero | |
| 5,178,606 A | 1/1993 | Ognier et al. | |
| 5,199,417 A | 4/1993 | Muller et al. | |
| 5,207,213 A | 5/1993 | Auhll et al. | |
| 5,237,984 A | 8/1993 | Williams et al. | |
| 5,269,756 A | 12/1993 | Dryden | |
| 5,313,934 A | 5/1994 | Wiita et al. | |
| 5,354,267 A | 10/1994 | Niermann et al. | |
| 5,413,092 A | 5/1995 | Williams, III et al. | |
| 5,419,309 A | 5/1995 | Biehl | |
| 5,439,022 A | 8/1995 | Summers et al. | |
| 5,486,155 A | 1/1996 | Muller et al. | |
| 5,505,707 A | 4/1996 | Manzie et al. | |
| 5,551,448 A | 9/1996 | Matula et al. | |
| 5,554,112 A | 9/1996 | Walbrink et al. | |
| 5,556,258 A | 9/1996 | Lange et al. | |
| 5,575,756 A | 11/1996 | Karasawa et al. | |
| 5,630,795 A | 5/1997 | Kuramoto et al. | |
| 5,797,836 A | 8/1998 | Lucey et al. | |
| 5,843,023 A * | 12/1998 | Cecchi | A61B 17/435 604/272 |
| 5,989,183 A | 11/1999 | Reisdorf et al. | |
| 6,110,103 A | 8/2000 | Donofrio | |
| 6,126,592 A | 10/2000 | Proch et al. | |
| 6,181,442 B1 | 1/2001 | Ogura et al. | |
| 6,282,442 B1 | 8/2001 | DeStefano et al. | |
| 6,354,813 B1 | 3/2002 | Laing | |
| 6,409,707 B1 * | 6/2002 | Guala | A61M 39/24 137/843 |
| 6,447,446 B1 | 9/2002 | Smith et al. | |
| 6,478,731 B2 | 11/2002 | Speier et al. | |
| 6,558,379 B1 | 5/2003 | Batchelor et al. | |
| 6,652,484 B1 | 11/2003 | Hunckler et al. | |
| 7,252,110 B2 | 8/2007 | Semeia | |
| 7,270,647 B2 | 9/2007 | Karpowicz et al. | |
| 7,413,542 B2 | 8/2008 | Kucklick et al. | |
| 7,708,689 B2 | 5/2010 | Deppmeier et al. | |
| 7,811,228 B2 | 10/2010 | Adams | |
| 8,001,984 B2 | 8/2011 | Sasaki | |
| 8,047,215 B1 | 11/2011 | Sasaki | |
| 8,079,952 B2 | 12/2011 | Fujimoto | |
| 8,231,574 B2 | 7/2012 | Haack et al. | |
| 8,337,470 B2 | 12/2012 | Prasad et al. | |
| 8,394,013 B2 | 3/2013 | Ichimura | |
| 8,419,624 B2 | 4/2013 | James et al. | |
| 2002/0120180 A1 | 8/2002 | Speier et al. | |
| 2004/0073088 A1 | 4/2004 | Friedman et al. | |
| 2005/0025646 A1 | 2/2005 | Miller et al. | |
| 2006/0041186 A1 | 2/2006 | Vancaillie | |
| 2006/0199998 A1 | 9/2006 | Akui et al. | |
| 2006/0264995 A1 | 11/2006 | Fanton et al. | |
| 2007/0213668 A1 | 9/2007 | Spitz | |
| 2008/0072970 A1 | 3/2008 | Gasser et al. | |
| 2008/0081948 A1 | 4/2008 | Weisenburgh et al. | |
| 2008/0200764 A1 | 8/2008 | Okada | |
| 2009/0234193 A1 | 9/2009 | Weisenburgh, II et al. | |
| 2009/0244223 A1 | 10/2009 | Mizutani et al. | |
| 2010/0198012 A1 | 8/2010 | Poole et al. | |
| 2011/0230716 A1 | 9/2011 | Fujimoto | |
| 2012/0316394 A1 | 12/2012 | Yoshida et al. | |
| 2013/0205936 A1 | 8/2013 | Schmieding et al. | |
| 2013/0211433 A1 | 8/2013 | Kadykowski et al. | |
| 2013/0289595 A1 | 10/2013 | Edwards et al. | |

FOREIGN PATENT DOCUMENTS

| | | |
|---|---|---|
| JP | H06/189893 A | 7/1994 |
| JP | 2005/040184 A | 2/2005 |
| JP | 2012/045325 A | 3/2012 |
| WO | 02/33296 A2 | 4/2002 |
| WO | 2012/069592 A1 | 5/2012 |

OTHER PUBLICATIONS

Potentially Related Application, U.S. Appl. No. 14/497,815, dated Sep. 26, 2014.
Potentially Related Application, U.S. Appl. No. 14/493,581, dated Sep. 23, 2014.
Potentially Related Application, U.S. Appl. No. 14/496,473, dated Sep. 25, 2014.
Potentially Related Application, U.S. Appl. No. 14/493,700, dated Sep. 23, 2014.
Potentially Related Application, U.S. Appl. No. 14/551,440, dated Nov. 24, 2014.
Potentially Related Application, U.S. Appl. No. 14/551,208, dated Nov. 24, 2014.

* cited by examiner

MULTI-WAY VALVE FOR A MEDICAL INSTRUMENT

FIELD

The present teachings relate generally to a valve, and more specifically to a multi-way valve for moving fluid between one or more fluid sources and a medical instrument.

BACKGROUND

Cleaning functions may be provided to or incorporated with certain medical instruments to help ensure that the instruments are clean, free of obstructions, and can operate properly during a medical procedure. For example, microdebriders may be used in medical procedures to cut, resect, and/or remove tissue, bone, or other bodily materials. After a period of time, however, the tissue, bone, or other bodily materials may accumulate and obstruct the microdebrider. Endoscopes may be used in medical procedures to gain visual access into an internal location of a patient. While an endoscope is positioned within the patient, however, a distal viewing end of the endoscope may be exposed to blood, tissue, fluid, debris, etc., which may obstruct visual access into the internal location of the patient. Accordingly, to maintain a clean medical instrument during a procedure, irrigation fluid, suction, or both may be provided to or incorporated with the instrument (including microdebriders and endoscopes), which typically requires connecting various individual cables, tubes, lines, ports, etc. to the instrument. The various individual cables, tubes, lines, ports, etc. connected to the medical instrument may however interfere with a doctor or surgeon performing the medical procedure, which may undesirable add additional time and/or complications to the procedure. Also, by connecting various individual cables, tubes, lines, ports, etc. to the medical instrument, selective application of irrigation fluid, suction, or both may be difficult to control. Therefore, it may be desirable to provide a valve that can combine and connect various individual cables, tubes, lines, ports, etc., to a single access point on a medical instrument and provide selective fluid communication between one or more fluid sources and the medical instrument.

It may be further desirable to provide a valve that is sufficiently sized (i.e., in relative size and weight) so that the valve does not interfere with or burden a doctor or surgeon performing a medical procedure. Further yet, it may be desirable to provide a valve including a disk, an occluder, and/or a membrane to provide selective communication between two or more fluid lines. In other words, it may be desirable to have a valve including a moving, deformable, and/or deflectable disk, occluder, and/or membrane so that the valve can be made with fewer components and can made smaller and lighter than a piston or ball valve, for example. U.S. Pat. Nos. 8,337,470, 5,439,022, 5,354,267, 7,270,647, and U.S. Pat. Pubs. US2006/0264995, 2013/0289595 and US2009/0244223 disclose various examples of supplying multiple cables, tubes, lines, ports, etc. to a single access point on a medical instrument, all of which are incorporated by reference herein in their entirety for all purposes.

SUMMARY

The present teachings provide a medical device comprising a first port; a second port in fluid communication with the first port; and a third port in selective fluid communication with both the first port and the second port; a sealing membrane disposed between the third port and both the first port and the second port, the sealing membrane is configured to move between a first position preventing fluid communication between the third port and both the first port and the second port and a second position allowing fluid communication between the third port and the first port, wherein movement of a fluid supplied to the medical device at the third port moves the sealing membrane from the first position to the second position.

The present teachings also provide a medical device comprising an instrument port; a suction port in fluid communication with the instrument port; and an irrigation port in selective fluid communication with both the instrument port and the suction port, the irrigation port is configured to be in communication with an irrigation source supplying fluid to the medical device; an occluder disposed between the irrigation port and both the instrument port and the suction port, the occluder is configured to move between a first position preventing fluid communication between the irrigation port and both the instrument port and the suction port and a second position allowing fluid communication between the irrigation port and both the instrument port and the suction port, when the occluder is in the second position a first portion of the fluid is configured to move from the irrigation port to the instrument port and a second portion of the fluid is configured to move from the irrigation port to the suction port, wherein movement of the fluid supplied to the medical device at the irritation port moves the occluder from the first position to the second position.

The present teachings further provide a valve that can combine and connect various individual cables, tubes, lines, ports, etc., to a single access point on a medical instrument. Further yet, the present teachings provide a valve providing selective fluid communication between one or more fluid sources and a medical instrument.

DETAILED DESCRIPTION

Figure 1:
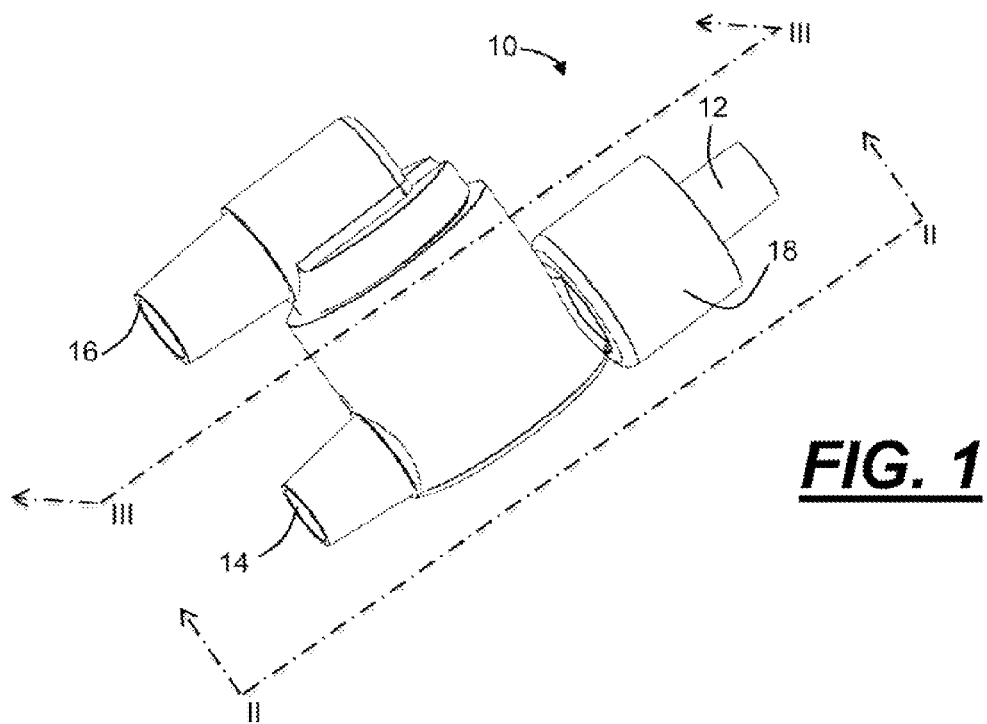
FIG. 1 illustrates a perspective view of a multi-way valve in accordance with the teachings herein.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide a system for use with a medical instrument, such as a microdebrider, an endoscope sheath, an endoscope, or a combination thereof. The system may include cleaning system, which may function to clean and protect a distal end of medical instrument. The cleaning system may function to clean an image sensor, a lens, or a device located at a distal viewing end of a medical instrument. The cleaning system may include one or more irrigation sources supplying, moving, communicating, transferring, or a combination thereof fluid such as an irrigation fluid to a medical instrument. The cleaning system may include one or more suction sources pulling, drawing, communicating, moving, or a combination thereof a fluid such as a vacuum and/or suction from or through a medical instrument. The one or more irrigation sources, suction sources, or both may be in constant communication, selective communication, or both with a medical instrument. The cleaning system may include one or more control modules.

The one or more control modules may function to control one or more of the irrigation sources, suction sources, medical instruments, or a combination thereof. The one or more control modules may function to control an amount of irrigation fluid, suction, or both supplied, applied, communicated, drawn, moved, and/or pulled to or from a medical instrument, an area or location of interest, a surgical site, or a combination thereof. The one or more control modules may control a running speed, a pumping duration, or both of the one or more pumps supplying irrigation fluid. The one or more control modules may control the order of application of irrigation fluid, suction, or both. The one or more control modules may function to stop a flow or movement of a fluid such as irrigation fluid or suction, apply a flow or movement of a fluid such as irrigation fluid or suction, or a combination thereof. The one or more control modules may include a power source, which may be electricity, battery, or both. The one or more control modules may include a microprocessor, a computer, a control algorithm, or a combination thereof. The one or more control modules may include one or more user interfaces, one or more pumps, one or more valves, or a combination thereof.

The one or more user interfaces may function to provide a user, such as a surgeon, doctor, or nurse, with the ability to monitor and/or control the system. The user interface may include one or more control knobs, buttons, switches, or selectors; one or more indicators; one or more user controls; one or more devices for adjusting, changing, or setting a system parameter or function; or a combination thereof. During use, for example, a user may activate and/or adjust one or more of the control knobs, buttons, indicators, controls, etc. to activate, control, adjust or a combination thereof one or more pumps, valves, system functions, or a combination thereof to start, stop, or change a system function, like an irrigation function, a suction function, or an application cycle.

The one or more pumps may function to supply, circulate, transfer, communicate, and/or move a fluid such as irrigation fluid from an irrigation source to a control module, a medical instrument, a multi-way valve, an irrigation port, or a combination thereof. The pump may supply, circulate, transfer, communicate, and/or move fluid with an impeller. The pump may function to create a negative pressure (e.g., suction or vacuum). Preferably, when the pump is activated, an amount of fluid is moved, which may be constant or may selectively vary. The pump may be a lobe pump, a centrifugal pump, a positive displacement pump, a rotary positive displacement pump, a diaphragm pump, a peristaltic pump, a rope pump, a gear pump, a screw pump, a progressing cavity pump, a roots-type pump, a plunger pump, or a combination thereof. Preferably, the pump is a peristaltic pump for supplying irrigation fluid to a multi-way valve through one or more irrigation lines.

The irrigation fluid may function to clean a medical instrument, an image sensor, a lens or device of a medical instrument, or a combination thereof. The irrigation fluid may function to move or flush particles, opaque fluids, contaminants, cut biological tissue, blood, obstructions, etc. or a combination thereof from a microdebrider, an endoscope sheath, an endoscope, an image sensor, a lens or device of an endoscope, a surgical site or a combination thereof. The irrigation fluid may function to clean an image sensor, a lens or device of an endoscope, or a combination thereof while the endoscope and endoscope sheath are in a patient. A fluid such as irrigation fluid may be supplied, circulated, transferred, communicated, and/or moved from an irrigation source. The irrigation fluid may be bioabsorbable. During an application cycle, the fluid may be supplied, applied, circulated, transferred, communicated, and/or moved to the multi-way valve, a medical instrument, or both continuously, selectively, intermittingly, or on-demand. Fluid movement, transfer, flow, communication etc. may function to move an occluder located within a multi-way valve from a first occluder position to a second occluder position. In the second occluder position, the irrigation port of the multi-way valve may be in communication with either or both of the instrument port and the suction port of the multi-way valve. When the occluder is in the second occluder position, the fluid may be supplied, circulated, transferred, communicated, and/or moved from the irrigation source, around the occluder to a suction source, a medical instrument, or both. A reduced or no flow or movement of the fluid may cause the occluder to move from the second position to the first position. In the first occluder position, the irrigation port is no longer in fluid communication, or at least partially not in communication with the instrument port and/or the suction port. The fluid may be supplied, circulated, transferred, communicated, and/or moved to the multi-way valve with a pump configured to pump the irrigation fluid at a pressure. The pressure of the fluid may change as the fluid reaches one or more of a multi-way valve, a medical instrument, an end of a medical instrument, an imaging lens or device, a viewing area, and a surgical site.

The irrigation fluid may be supplied via a gravity feed, and thus, the pressure of the irrigation fluid may be determined by the height of an irrigation source. For example, a vertical placement height of an irrigation source may determine the amount of pressure and/or force the irrigation fluid applies to a distal end of a medical instrument. The pressure of the irrigation fluid may be sufficiently high so that a flow director located at a distal end of a medical instrument may redirect the irrigation fluid. The irrigation fluid may be supplied, circulated, transferred, communicated, and/or moved with a sufficient amount of pressure so that the surface tension of the irrigation fluid wicks across a distal end, an image sensor, lens or device, or a combination thereof of a medical instrument (e.g., the pressure may be low enough that the irrigation fluid remains in contact with an endoscope sheath, an endoscope or both). The pressure may be low so that the flow of irrigation fluid is laminar across a medical instrument. The irrigation fluid may be applied with a pressure of about 0.10 MPa or more, about 0.20 MPa or more, about 0.30 MPa or more, or even about 0.50 MPa or more. The irrigation fluid may be applied with a pressure of about 3 MPa or less, about 2 MPa or less, about 1 MPa or less, or even about 0.75 MPa or less. The pressure of the irrigation fluid may be varied based on a size, length, or both of an irrigation line extending between an irrigation source and a multi-way valve, a medical instrument, or both.

The one or more irrigation lines may function to connect an irrigation source, a pump, or both to a multi-way valve, a medical instrument, or both. The one or more irrigation lines may be one or any number of lines supplying, circulating, transferring, communicating, and/or moving a fluid such as irrigation fluid from an irrigation source, a pump, a valve, or a combination thereof to a multi-way valve, a medical instrument, or both. The one or more irrigation lines may function to assist in creating a pressure head so that the irrigation fluid is supplied, circulated, transferred, communicated, and/or moved to move, remove, or flush particles, opaque fluids, contaminants, cut biological tissue, blood, obstructions, or a combination thereof from a point of interest, a medical instrument, a microdebrider, an endoscope sheath, an endoscope, an image sensor, a lens or device of an endoscope, a surgical site, or from a combination thereof. The one or more irrigation lines may be elongated rigid, flexible, or movable tubes or conduits, or a combination thereof. The one or more irrigation lines may be made of a material suitable for use in surgical procedures. At one end, the one or more irrigation lines may be connected to an irrigation source, and at the other end the one or more irrigation lines may be connected to an irrigation port, a suction port, or an instrument port of the multi-way valve. The one or more irrigation lines may connect a suction source to a multi-way valve, a medical instrument, or both (i.e., suction may be supplied through the irrigation lines).

The suction source may function to move, remove, or flush particles, opaque fluids, contaminants, cut biological tissue, blood, obstructions, irrigation fluid, or a combination thereof from a medical instrument, a point of interest, a surgical site, or from a combination thereof. The suction source may function to perform a drying function, remove fluid spots, remove contaminants, or a combination thereof. The suction source may be a pump, reversal of a motor, a common suction source, a hospital suction source or a combination thereof. The suction source may be configured to pull, move, communicate and/or draw a sufficient amount of a fluid such as vacuum or suction through one or more suction lines, irrigation lines, or both to remove a predetermined amount of fluid in a predetermined amount of time. For example, the suction source may pull or draw fluid such as a vacuum or suction so that 10 ml of irrigation fluid is removed in 1 to 2 seconds. The suction source may pull, move, communicate and/or draw a vacuum or suction that is continuous, selective, on-demand, or a combination thereof through one or more suction lines.

The one or more suction lines may function to connect a suction source to a multi-way valve, a medical instrument, or both. At one end, the one or more suction lines may be connected to a suction source, and at the other end the one or more suction lines may be connected to an irrigation port, a suction port, or an instrument port of the multi-way valve. The one or more suction lines may be one or more lines so that a fluid, suction or vacuum may be pulled, moved, communicated and/or drawn from by suction source from a multi-way valve, an imaging lens or device, a medical instrument, or a combination thereof. The one or more suction lines may function to assist in pulling, moving, communicating, and/or drawing a fluid, vacuum or suction at or near a distal end of medical instrument. The one or more suction lines may be elongated rigid, flexible, movable tubes conduits or a combination thereof. The one or more suction lines may be made of a material suitable for use in surgical procedures to pull, draw or move fluid, vacuum, and/or suction. The one or more suction lines may also connect an irrigation source, a pump, a valve, or a combination thereof to one or more multi-way valves, medical instruments, or both. (i.e., irrigation may be supplied through the suction lines). The suction lines and the irrigation lines may be the same line or may be different lines. The suction line, the irrigation line, or both may be connected to a multi-way valve for connecting the suction line, the irrigation line, or both to a medical instrument via a valve adapter.

The valve adapter may function to deliver, supply, apply, remove, or a combination thereof fluid such as irrigation fluid, suction, or both between an irrigation source, a suction source, a multi-way valve, or combination thereof and a medical instrument such as an endoscope, an endoscope sheath, a microdebrider, or a combination thereof. The valve adapter may be or may provide a single access point between the multi-way valve and a medical instrument. The valve adapter may have an increased cross-sectional area (e.g., diameter) relative to a cross-sectional area of an irrigation line, a suction line, a multi-way valve, or a combination thereof. The valve adapter may be the same size as the irrigation lines, suction lines, the multi-way valve or a combination there. The valve adapter may be in fluid communication with an instrument port of a multi-way valve. The valve adapter may include a coupling, a fitting, a quick-connect feature, a flared port, an O-ring port, a tapered port, a threaded port or a combination thereof. The valve adapter may function to deliver one or more fluids to a medical instrument during an application cycle.

The application cycle may function to clean and protect a medical instrument, such as an endoscope sheath, an endoscope, an image sensor, lens or device of an endoscope, an area or location of interest, a surgical site, or a combination thereof. The application cycle may be sufficiently long so that an image sensor, lens or device of a medical instrument is cleaned and good images can be obtained therewith. The application cycle may be a cycle where a one or a combination of different applications, cycles, sequences, and/or functions are applied or performed. The application cycle may be a cycle where irrigation fluid and suction are applied simultaneously, in sequence, intermittingly, on-demand, or in a combination thereof, to clean a medical instrument. The application cycle may include an application of irrigation fluid followed immediately by an application of suction. The application cycle may apply a concurrent application of irrigation fluid and suction. Irrigation fluid may be supplied from an irrigation fluid source to a multi-way valve, which may direct, move, communicate, and/or transfer the irrigation fluid through the multi-way valve to a medical instrument. A suction source connected to the multi-way valve may simultaneously, or subsequently, draw, pull, move, and/or communicate suction from the medical instrument to help remove the irrigation fluid, the blood, tissue, and other obstructions from the distal end thereof. The application cycle may include only an application of irrigation fluid (i.e., a flushing cycle, a washing manner, etc.) with no suction. The application cycle may include only an application of suction with no application of irrigation fluid. The application cycle may be varied, adjusted, monitored, and/or controlled by a user, by one or more control modules, user interfaces, or a combination thereof. For example, a user may pre-set an application cycle so that one touch of a switch causes irrigation fluid to run for 5 seconds.

The multi-way valve may function to connect and/or provide fluid communication between one or more suction lines, irrigation lines, or both and a single access point, a common line, a valve adapter, a medical instrument, or a combination thereof. The multi-way valve may function to direct or provide a path for fluid, suction, or both to move between an irrigation source, a suction source, a control module, or a combination thereof, and a single access point, a common line, a valve adapter, a medical instrument, or a combination thereof. The multi-way valve may function to allow a suction function, an irrigation function, or both to work at a given time. For example, the multi-way valve may function to block the transfer of irrigation fluid or suction so that only suction or only irrigation fluid, respectively, can be applied to a medical instrument, a common line, a valve adapter, or a combination thereof. The multi-way valve may function to allow a suction function and an irrigation function to be applied simultaneously to a medical instrument, a common line, a valve adapter, or a combination thereof. The multi-way valve may include two or more lines, or even three, four, or five or more lines. The multi-way valve may include two or more ports, preferably three or more ports, four, or even five or more ports. The multi-way valve may be connected to one or more fluid lines, two or more fluid lines, preferably three or more fluid lines, four, or even five or more fluid lines. The multi-way valve may function to consolidate fluid from two or more sources and/or lines into a single line and then direct, supply, apply, move, or provide for the transfer of the fluid between the two or more lines and a common line, a single access point, a valve adapter, a medical instrument, or a combination thereof. The multi-way valve may be fabricated from a material having strength properties suitable for use in medical procedures to receive, block, transfer, supply, move, draw, communicate and/or redirect irrigation fluid, suction, or both to a medical instrument. The multi-way valve may include a primary line.

The primary line may function to provide a fluid path or passageway between a suction source, an irrigation source, a control module, or a combination thereof and a common line, a valve adapter, a medical instrument, or a combination thereof. The primary line may be in fluid communication or in selective fluid communication with a secondary line, an irrigation source, a suction source, a control module, or a combination thereof. The primary line may function to provide for the transfer, supply, movement, direction, re-direction, or a combination thereof of fluid between a secondary line, an irrigation source, a suction source, a control module, or a combination thereof and a common line, a valve adapter, a medical instrument, or a combination thereof. The primary line may function to provide for the transfer, supply, movement, direction, re-direction, or a combination thereof of irrigation fluid, suction, or both individually or together between a valve adapter, a medical instrument, or both and an irrigation source, a suction source, or both. The primary line may be fabricated from a material capable of withstanding flow or movement of irrigation fluid, suction, or both. The primary line may function to provide irrigation fluid, suction or both to a medical instrument so that obstructions such as blood, tissue, fluid, debris, etc. can be cleaned from a distal viewing end. The primary line may provide a pathway for fluid to move along a suction path from the instrument port to the suction port. The primary line may provide a pathway for fluid to move or flow to the instrument port; move or flow to the suction port; or both. The primary line may provide a pathway for obstructions to be moved or removed from the medical instrument to the suction source. The primary line may include an instrument port.

The instrument port or the first port may function to provide an outlet, an inlet, a coupling, a connection, an orifice or a combination thereof between the multi-way valve and a medical instrument, a valve adapter, a common line, a single access port, or a combination thereof. The instrument port may include a coupling, a fitting, a quick-connect feature, a flared port, an O-ring port, a tapered port, a threaded port, or a combination thereof to connect the multi-way valve to a valve adapter, a medical instrument, a common line, or a combination thereof. The instrument port may be in communication or in selective communication with an irrigation source, a suction source, a control module, or a combination thereof. The instrument port may be in communication or in selective communication with an irrigation port, a suction port, the primary line, a secondary line, a flange, or a combination thereof. The instrument port may be integrally formed with the primary line, or may be coupled thereto with mechanical fasteners.

The irrigation port may function to provide an outlet, an inlet, a coupling, a connection, a connection point, an orifice or a combination thereof between the multi-way valve and a suction source, an irrigation source, a control module, or a combination thereof. The irrigation port may include a coupling, a fitting, a quick-connect feature, a flared port, an O-ring port, a tapered port, a threaded port or a combination thereof to connect the multi-way valve, the primary line, or both to an irrigation source, a suction source, a control module, or a combination thereof. The irrigation port may be in communication or in selective communication with an irrigation source, a suction source, a control module or a combination thereof. The irrigation port may be in fluid communication or in selective fluid communication with a suction port, an instrument port, the primary line, a secondary line, or a combination thereof. The irrigation port may be integrally formed with the secondary line or may be coupled thereto with mechanical fasteners.

The suction port may function to provide an outlet, an inlet, a coupling, a connection, a connection point, an orifice or a combination thereof between the multi-way valve and a suction source, an irrigation source, a control module, or a combination thereof. The suction port may include a coupling, a fitting, a quick-connect feature, a flared port, an O-ring port, a tapered port, a threaded port or a combination thereof to connect the multi-way valve, the primary line, or both to an irrigation source, a suction source, a control module, or a combination thereof. The suction port may be in communication or in selective communication with an irrigation source, a suction source, a control module or a combination thereof. The suction port may be in fluid communication or in selective fluid communication with an irrigation port, an instrument port, the primary line, a secondary line, or a combination thereof. The suction port may be integrally formed with the primary line or may be coupled thereto with mechanical fasteners. A manifold may be located between suction port and the instrument port.

The manifold may function to provide fluid communication between the instrument port and the suction port, the irrigation port and the suction port, the irrigation port and the instrument port, and/or any instruments and/or devices connected to any of the aforementioned ports. The manifold may be located at least partially within the primary line, at least partially within the flange, at least partially within the secondary line, or a combination thereof. The manifold may include a first aperture providing communication to the instrument port. The manifold may include a second aperture providing communication to the suction port. The manifold may include a third aperture providing fluid communication between the primary line the secondary line, the flange, or both. The manifold may include a passageway providing communication between the irrigation port and the suction port, the instrument port and the suction port, or a combination thereof. The passageway may be located in or through a stalk, in a flange, or both. The first aperture may be larger than the second aperture, the third aperture, or both. The first aperture may be smaller than the second aperture, the third aperture, or both. The first aperture may be the same size as the second aperture, the third aperture, or both. The manifold may direct or provide for a larger volume of fluid to communicate from the secondary line to the instrument port compared to a volume of fluid communicated from the secondary line to the suction port. The manifold may include a cross-sectional area that is generally smaller than the primary line, or may be the same size. The manifold may provide communication between the primary line and the secondary line. A ring baffle may at least partially restrict a flow of fluid communicating from the irrigation port to the suction port.

The ring baffle may function to prevent some or all of a back flow of fluid through the multi-way valve. The ring baffle be located downstream of an occluder. The ring baffle may function to prevent at least a portion of irrigation fluid, suction, or both from flowing to the suction port, the suction source, the irrigation port, the irrigation source, or a combination thereof. The ring baffle may be rigid, deformable, flexible, undulating, or a combination thereof. The ring baffle may be disposed around a center stalk; fit or disposed within a groove around a stalk; fit or disposed within a flange; or a combination thereof. The ring baffle may include a center opening so that the ring baffle can fit around at least a portion of a center stalk. The ring baffle may touch and/or engage a flange, or may be at least partially spaced away therefrom. The ring baffle may at least partially deflect when fluid, irrigation fluid, suction, or a combination thereof moves, flows, communicates, is transferred, is drawn, or a combination thereof through the multi-way valve. The ring baffle may provide for one-way flow of irrigation fluid, suction, or both through one or more of the primary line, the secondary line, the multi-way valve, or a combination thereof.

The secondary line may function to provide a path or passageway between an irrigation source, a suction source, a control module or a combination thereof and a flange, a primary line, a common line, a valve adapter, a medical instrument, or a combination thereof. The secondary line may be in communication or in selective communication with a flange, a primary line, a valve adapter, a medical instrument, or a combination thereof. The secondary line may be fabricated from a material capable of withstanding a flow, movement, transfer, drawing, or a combination thereof of fluid such as irrigation fluid, suction, or both. The secondary line may function to direct or provide for the communication, transfer, supply, and/or movement of fluid from an irrigation source, a suction source, a control module, or a combination thereof to a primary line, a valve adapter, a medical instrument, or a combination thereof. The secondary line may function to direct or provide irrigation fluid to move along a path of fluid flow from the irrigation port to the instrument port so that obstructions such as blood, tissue, fluid, debris, etc. can be cleaned from a distal viewing end a medical instrument. The secondary line may function to direct or provide irrigation fluid to move along main irrigation fluid path from the irrigation port to the flange, the instrument port, the suction port or both. The secondary line may be integrally formed with a primary line, a flange, or both. The secondary line may be selectively coupled, removably coupled or rigidly coupled to the flange, the primary line, or both with one or more mechanical fasteners such as adhesives, bolts, screws, quick release connections, or a combination thereof. The secondary line may include a second threaded portion configured to threadably engage a flange.

The flange may function to create a connection between the secondary line and a primary line. The flange may function to direct fluid such as irrigation fluid, suction, or both from an irrigation source, an irrigation port, a secondary line, or a combination thereof to a primary line, a suction port, an instrument port, a common line, a valve adapter, a medical instrument, or a combination thereof. The flange may be integrally formed with one or both of the secondary line and the primary line. The flange may be coupled, selectively coupled, removably coupled or rigidly coupled to the primary line, the secondary line, or both using one or more mechanical fasteners such as adhesives, bolts, screws, quick release connections, or a combination thereof. The flange may include a first threaded portion configured to threadably engage a mating second threaded portion on the secondary line. A seal, such as a gasket, an O-ring, thread tape, or a combination thereof may be disposed between the first and second threaded portions to ensure a fluid seal there between. The flange may include a stalk.

The stalk may function to direct fluid such as irrigation fluid, suction, or both from the secondary line to the primary line. The stalk may function to direct fluid such as irrigation fluid, suction, or both from the irrigation port to the instrument port, the suction port, or both. The stalk may be tapered or cone shaped. The stalk may be integrally formed with the flange, the primary line, the secondary line, or a combination thereof. The stalk may be mechanically coupled or attached to one or more of the primary line, the secondary line, the flange, or a combination thereof. The stalk may include a passageway that may function to create and/or maintain an area of low pressure, which may help establish and/or maintain suction between an instrument port and a suction port, a suction source, or both. The passageway may be the third opening in the manifold providing communication between the instrument port and the suction port, and/or the irrigation port and the suction port. The stalk may be integrally formed with the flange, or may be mechanically connected thereto. The stalk may be fabricated from a material capable of withstanding and/or directing irrigation fluid, suction, or both. The stalk may include a groove for receiving the ring baffle. The stalk may engage an occluder when the occluder is in the first occluder position and the second occluder position. The stalk may include a stalk tip.

The stalk tip may function to engage or selectively engage the occluder when the occluder is in the first occluder position, the second occluder position, or both. The stalk tip may engage the downstream surface of the occluder when the occluder is in the first occluder position, the second occluder position, or both. The stalk tip may engage a generally central portion of the downstream surface of the occluder. The stalk tip may engage the downstream surface of the occluder so that when the occluder moves from the first occluder position to the second occluder position, the occluder bends or deforms about or around the stalk tip. When the occluder is in the first occluder position, the stalk tip may engage the downstream surface and support the occluder so that at least a portion of the upstream surface is biased, pushes against and/r engages at least a portion of the upstream sealing surface.

The upstream sealing surface may function to cooperate with the occluder to provide selective communication between the secondary line and the flange, the primary line, a medical instrument, or a combination thereof. The upstream sealing surface may function to cooperate with the occluder to provide selective communication between the irrigation port and the suction port, the irrigation port and the instrument port, or both. The upstream sealing surface may be integrally formed with one or more of the secondary line, the flange, and the primary line. The upstream sealing surface may be mechanically coupled to the secondary line, the flange, or both using mechanical fasteners. The upstream sealing surface may include a cross section that is generally circular, or a cross section that has a different shape such as rectangular or ovoid shape for example. The upstream sealing surface may include a central opening. The occluder may engage at least a portion of the upstream sealing surface when the occluder is in the first occluder position. At least a portion of the occluder may move, deflect, bend, or a combination thereof away from the upstream sealing surface in the second occluder position providing fluid communication between the secondary line and the primary line. One or more downstream retaining surfaces may be located oppose the upstream sealing surface.

The one or more downstream retaining surfaces may cooperate with the occluder, the upstream sealing surface, and/or the chamber walls to provide selective fluid communication between the secondary line and the primary line. The one or more downstream retaining surfaces may cooperate with the occluder, the upstream sealing surface, and/or the chamber walls to provide selective fluid communication between the irrigation port and the instrument port, the irrigation port and the suction port, or both. The one or more downstream retaining surfaces may extend radially from the chamber wall. The one or more downstream retaining surfaces may extend towards the central opening of the flange. At least a portion of the occluder may engage one or more downstream retaining surfaces when the occluder is in the first occluder position, the second occluder position, or in a position in between. One or more surface passages may be disposed intermediate one or more of the one or more downstream retaining surfaces. One or more of the one or more wall passages may be generally aligned with one or more of the one or more surfaces passages so that fluid can communicate there through when the occluder is in the first position, the second position, or in a position in between. The one or more downstream retaining surfaces and the one or more surface passages may be equally spaced about a central opening, or may be randomly disposed thereabout.

The one or more downstream retaining surfaces, the one or more surface passages, or both may each be generally the same size, or the sizes may vary. The one or more surfaces passages may function to provide fluid communication between the secondary line and the primary line when the occluder is in a first occluder position, a second occluder position, or an occluder position in between.

The chamber wall may function to cooperate with the occluder, the upstream sealing surface, and the one or more downstream retaining surfaces to provide selective fluid communication between the secondary line and the primary line. The chamber wall may be integrally formed with or attached to one or more of the secondary line, the primary line, the flange, the upper sealing surface, and the downstream retaining surfaces. The chamber wall may include a cross section that matches the upper sealing surface, the one or more lower sealing surfaces, or both. The chamber wall may be integrally formed with the upstream sealing surface, the one or more downstream retaining surfaces, or both. The chamber wall may include one or more wall passages.

The one or more wall passages may function to provide fluid communication between the secondary line and the primary line. The one or more wall passages may function to provide fluid communication between the secondary line and the primary line when the occluder is in the first occluder position, the second occluder position, or in a position in between. The one or more wall passages may be equally spaced about a central opening of the upstream sealing flange, or may be randomly spaced thereabout. One or more of the one or more wall passages may be of the same size or may vary in size. One or more of the one or more wall passages may be generally aligned with one or more of the one or more surfaces passages so that fluid can communicate there through when the occluder is in the first occluder position, the second occluder position, or in a position in between.

The occluder may be a disk, a membrane, a sealing membrane, or a combination thereof and may function to provide selective fluid communication between the secondary line and the primary line. A valve including a membrane may provide for a smaller valve than a valve including a disk. The occluder may function to selectively create and block fluid communication between the irrigation port and either or both of the instrument port and the suction port. The occluder may be permeable or, preferably, non-permeable. The occluder may be rigid, pliable, thin, preferably very thin, planar, circular, dome-shaped, a half-circle, a rectangle, may include a constant or variable wall thickness and/or cross section, or a combination thereof. The occluder may be made in most any shape, but may preferably matches the shape of the chamber, the upper sealing surface, the downstream sealing surface, or a combination thereof. The occluder may function to translate, deform, deflect, crinkle, ripple, form undulations, move, or a combination thereof when subjected to a flow or movement of a fluid, such as an irrigation fluid, suction, or both. The occluder may be elastically deformable with memory so that after the occluder translates, deforms, deflects, crinkles, ripples, forms undulations, moves, or a combination thereof, the occluder can go back to its original configuration. The occluder may be fabricated from a material suitable for use with irrigation fluid, suction, or both. The occluder may translate, deform, deflect, crinkle, ripple, form undulations, move, or a combination thereof from a first occluder position where fluid is restricted or prevented from communicating between the secondary line and the primary line to a second occluder position where fluid can communicate between the secondary line and the primary line. The occluder may translate, deform, deflect, crinkle, ripple, form undulations, move, or a combination thereof to a position between the first occluder position and the second occluder position to provide a reduced or at least some fluid communication between the secondary line and the primary line. The occluder may function to provide fluid communication between one or more devices and/or medical instruments (e.g., an irrigation source, a suction source, an endoscope, an endoscope sheath, a microdebrider, a control module, etc.) connected to any of the instrument port, the irrigation port and the suction port. The occluder may include an upstream surface and a downstream surface. The upstream surface, the downstream surface, or both may include a resilient or biasing material. At least a portion of the upstream surface may engage the upper sealing surface of the upstream sealing flange when the occluder is in the first occluder position. At least a portion of the downstream surface may engage the downstream retaining surface, the stalk, the stalk tip, or a combination thereof.

In the first occluder position, the occluder may function to at least partially or completely restrict, prevent and/or block fluid communication between the irrigation port, the secondary line, or both and the flange, the primary line, the medical instrument, the suction source, or a combination thereof. In the first occluder position, at least a portion of the occluder may engage or be in communication with the upstream sealing surface. In the first occluder position, an upstream face of the occluder may engage at least a portion of the upstream sealing surface. In the first occluder position, fluid may be restricted, prevented, and/or blocked from moving, communicating or flowing around the occluder; moving, communicating, or flowing through the occluder, moving, communicating, or flowing through the wall passages; moving, communicating, or flowing though the surface passages; moving, communicating, or flowing through the flange; or a combination thereof. The occluder may move axially between the upstream sealing surface and the downstream retaining surfaces, radially in the chamber wall, or both when the occluder is in the first occluder position, translating, deforming, deflecting, crinkling, rippling, forming undulations, moving, or a combination thereof from the first occluder position to the second occluder position, and/or translating, deforming, deflecting, crinkling, rippling, forming undulations, moving, or a combination thereof from the second occluder position to the first occluder position. A reduced or zero flow, movement, or communication of fluid from the irrigation port may function to translate, undeform, un-deflect, un-crinkle, un-ripple, move, remove undulations, or a combination thereof, the occluder to the first occluder position. In the first occluder position, the downstream face of the occluder may engage a stalk tip, which may function to bias the upstream face of the occluder against the upstream sealing surface. A biasing member, such as a spring or a resilient or biasing material, may be located or disposed on the downstream face of the occluder.

The biasing member may function to move, decompress, translate, expand, or a combination thereof when a reduced or no-flow fluid condition is realized in the secondary line, the irrigation port, or both so that the occluder can translate, undeform, un-deflect, un-crinkle, un-ripple, remove or un-form undulations, move, or a combination thereof from the second position to the first position. The biasing member may function to move or bias the upstream face of the occluder against the upstream sealing surface when the occluder is in the first occluder position. The biasing member may be a spring, a resilient or biasing material, an elastic member, or a combination thereof. The biasing member may be located on the downstream face of the occluder, the stalk, stalk tip, the one or more downstream lower surfaces, or on a combination thereof. In the first occluder position, fluid may communication in the primary line along a suction path.

The suction path may function to be a path for fluid to communicate between the instrument port and the suction port via the primary line. The suction path may be a path for irrigation fluid, suction, or both to communication through the primary line. The suction path may be a path for irrigation fluid, suction, or both to communicate from the instrument port, around a ring baffle, down a passage, and to the suction port. The suction path may be a path for irrigation fluid, suction, or both to communicate from the instrument port, through the first aperture and through the second aperture to the suction port. The suction path may be a path for fluid communication between the instrument port and the suction port when the occluder is in the first occluder position, the second occluder position, or in a position therebetween.

In the second occluder position, the occluder may function to provide communication between the secondary line and the flange, the primary line, or both. In the second occluder position, at least a portion of the occluder may engage or be in communication with the one or more downstream retaining surfaces. In the second occluder position, at least a portion of the occluder may be separated from the upstream sealing surface. Flow, communication, transfer, and/or movement of a fluid may translate, deform, deflect, crinkle, ripple, form undulations, move, or a combination thereof at least a portion of the occluder from the first occluder position to the second occluder position so that fluid can communicate from the secondary line to the primary line. The occluder may form one or more undulations when the occluder moves from the first occluder position to the second occluder position. Movement or flow of fluid may cause the occluder to bend or deform about a stalk located between the secondary line and the primary line. In second occluder position, at least a portion of the fluid can move, communicate, or flow through the one or more wall passages; move, communicate, or flow through the one or more surface passage; move, communicate, or flow through the undulations; move, communicate, or flow around the occluder; and/or move, communicate, or flow into the flange, the line, and/or the primary line. The occluder may uniformly translate from the first occluder position to the second occluder position. In order words, the occluder may move or translate from the first occluder position to the second occluder position without, bending, deforming, deflecting, crinkling, rippling, forming undulations, or a combination thereof. The occluder may also move and/or translate from the first occluder position to the second occluder position while also bending, deforming, deflecting, crinkling, rippling, forming undulations, or a combination thereof. In another configuration, the occluder may deflect, bend, fold, crinkle, form undulations, or a combination there of, but not move or translate when moving from the first occluder position to the second occluder position. The occluder may move axially in the flange, radially in the flange, or both when the occluder is in the first occluder position, the second occluder position, or both, and/or when moving, translating, deforming, deflecting, crinkling, rippling, forming undulations, or a combination thereof between the first occluder position and the second occluder position.

The main irrigation fluid path may be a path for fluid to move, communicate, transfer and/or be drawn from the irrigation port, the irrigation source, the secondary line, or a combination thereof to the primary line, the instrument port, the suction port, or a combination thereof. The main irrigation fluid path may be a path for irrigation fluid, suction, or both to move, communicate, transfer and/or be drawn from the secondary line to the primary line when the occluder is in the first occluder position, the second occluder position, or a position therebetween. The main irrigation fluid path may include a first portion irrigation fluid path and a second portion irrigation fluid path.

The first portion irrigation fluid path may be a path for fluid to move, communicate, transfer and/or be drawn from the irrigation port, the irrigation source, the secondary line, or a combination thereof to the primary line, the instrument port, or both. The first portion irrigation fluid path may be a path for fluid to move, communicate, transfer and/or be drawn from the secondary line to the primary line when the occluder is in the second occluder position, the first occluder position, or a position in between. The first portion irrigation fluid path may be a path for fluid to move, communicate, transfer and/or be drawn from the irrigation port to the first aperture of the manifold. The fluid in the first portion irrigation fluid path may move, communicate, and/or transfer from main irrigation fluid path and flow around the occluder, or past undulations formed in the occluder ring baffle, through one or more wall passages, surface passages, or both, down the flange, through the first aperture and to a medical instrument connected to the instrument port. The first portion irrigation fluid path may be a path for irrigation fluid, suction, or both that includes a volume of fluid that is larger, smaller or the same as a volume of fluid in a second portion irrigation fluid path.

The second portion irrigation fluid path may be a path for fluid to move, communicate, transfer and/or be drawn from the irrigation port, the irrigation source, the secondary line, or a combination thereof to the primary line, the suction port, or both. The second portion irrigation fluid path may be a path for fluid to move, communicate, transfer and/or be drawn from the secondary line to the primary line when the occluder is in the second occluder position, the first occluder position, or a position in between. The second portion irrigation fluid path may be a path for fluid to move, communicate, transfer and/or be drawn from the irrigation port, around the occluder and/or past the undulations formed in the occluder, through the one or more wall passages and surface passages, through the second aperture to a suction source connected to the suction port of the multi-way valve. The first portion irrigation fluid path may be a path of irrigation fluid, suction, or both that may include a volume of fluid that is larger, smaller or the same as a volume of fluid in a first portion irrigation fluid path.

FIG. 1 illustrates a multi-way valve 10. The multi-way valve 10 includes an instrument port 12 (i.e., a first port), a suction port 14 (i.e., a second port), and an irrigation port 16 (i.e., a third port). The instrument port 12 is in communication with the suction port 14 and in selective communication with the irrigation port 16. The irrigation port 16 is in selective communication with the suction port 14. The multi-way valve 10 includes a Luer fitting 18 located near the instrument port 12 to connect the multi-way valve 10 to the valve adapter 92, the medical instrument 83, or both.

Figure 2:
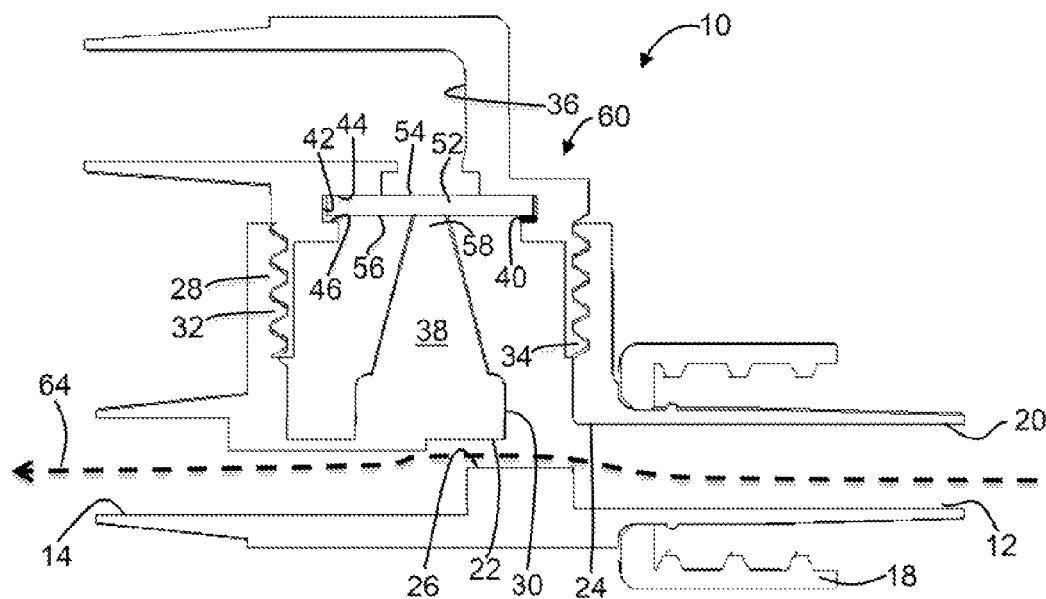
FIG. 2 illustrates a cross-sectional view of the multi-way valve of FIG. 1 cut along line II-II in accordance with the teachings herein.

FIG. 2 illustrates a cross-sectional view of the multi-way valve 10 taken along line II-II of FIG. 1. A primary line 20 extends between the instrument port 12 and the suction port 14. The Luer fitting 18 is located on the primary line 20 near the instrument port 12 and prevents a back-flow of fluid into the primary line 20. The main line 20 includes a manifold 22 located between the instrument port 12 and the suction port 14. The manifold 22 includes a first aperture 24 in communication with the instrument port 12, a second aperture 26 in communication with the suction port 14, and a third aperture 30 in communication with a flange 28. The flange 28 includes a first threaded portion 32 threadably engaging a mating second threaded portion 34 on a secondary line 36. A stalk 38 including a stalk tip 58 is located in the flange 28. The multi-way valve 10 includes an upstream sealing surface 44, a downstream retaining surface 46, and a chamber wall 42 disposed therebetween. An occluder, disk or sealing membrane 52 is located between the upstream and downstream surfaces 44, 46. The occluder 52 includes an upstream face 54 and an opposing downstream face 56. When the occluder 52 is in a first occluder position 60, the stalk tip 58 engages the downstream face 56 and retains the upstream face 54 of the occluder 52 against the upstream sealing surface 44. A biasing member 40 is configured to bias the upstream face 54 against the upstream sealing surface 44. When the occluder 52 is in the first occluder position 60, a suction source 74 (See FIG. 8) connected to the suction port 14 can draw or communicate suction through the primary line 20 along a suction path 64 extending from the instrument port 12 to the suction port 14.

Figure 3:
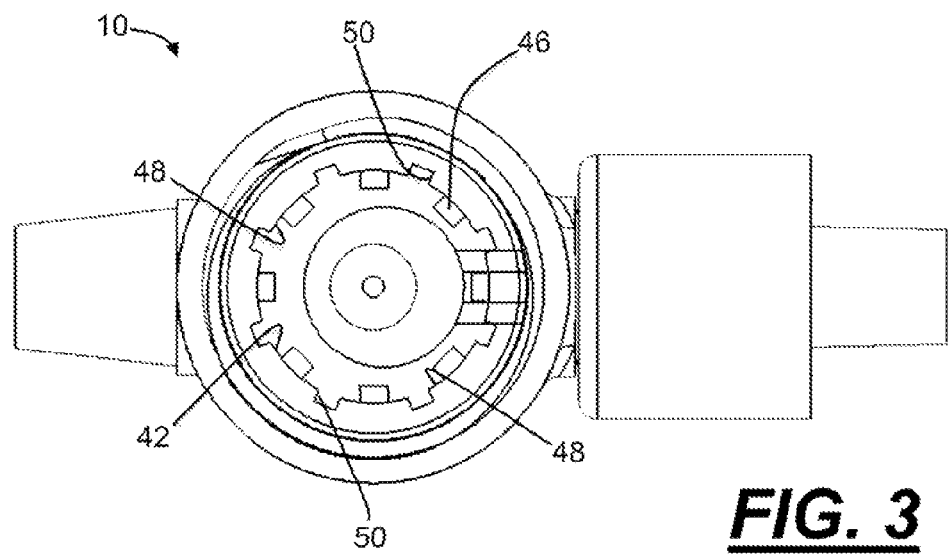
FIG. 3 illustrates a cross-sectional view of the multi-way valve of FIG. 1 cut along line III-III in accordance with the teachings herein.

FIG. 3 illustrates a cross-sectional view of the multi-way valve 10 taken along line III-III of FIG. 1. The chamber wall 42 includes a plurality of wall passages 50. The downstream retaining surface 46 includes a plurality of surface passages 48. When the occluder 52 is in the second occluder position 62, fluid can communicate from the secondary line 36 to the primary line 20 through the surface passages 48 and the wall passages 50

Figure 4:
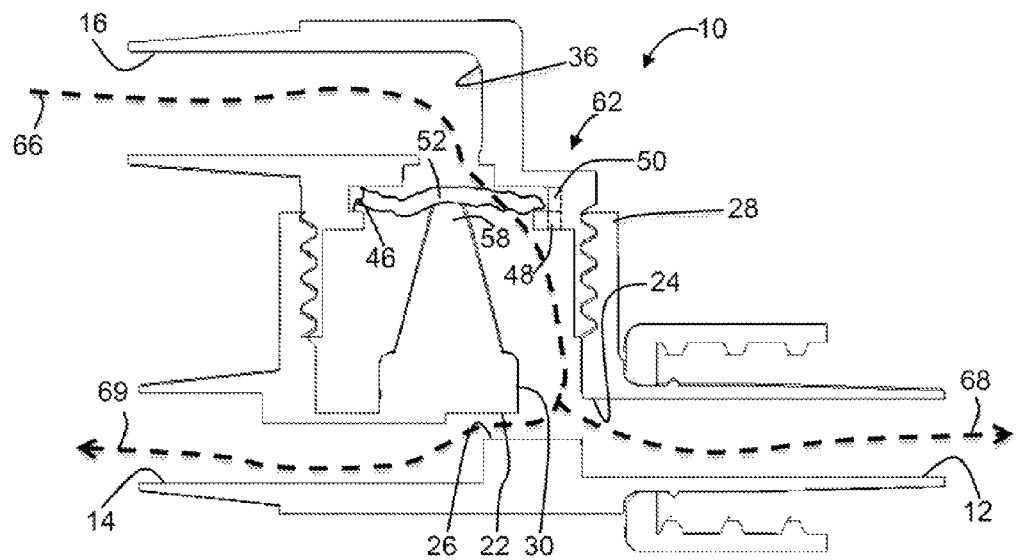
FIG. 4 illustrates a cross-sectional view of a multi-way valve of FIG. 1 cut along line II-II in accordance with the teachings herein.

FIG. 4 illustrates a cross-sectional view of the multi-way valve 10 taken along line II-II of FIG. 1. An irrigation source 72 (See FIG. 8) connected to the irrigation port 16 can supply irrigation fluid to the secondary line 36 along a main irrigation fluid path 66. Movement the irrigation fluid causes at least a portion of the occluder, disk, and/or membrane 52 to move, translate, bend, deflect, deform, crinkle, ripple, and/or form undulations as the occluder 52 moves further against the stalk tip 58 towards the downstream retaining surface 46 to the second occluder position 62. The irrigation fluid moves or communicates along the main irrigation fluid path 66, around deformations formed in the occluder 52, through the wall passages 50 and surface passages 48 (See also FIG. 5, for example) and into the flange 28. The irrigation fluid then moves through the third aperture 30 in the manifold 22 where a first portion of the irrigation fluid moves through the first aperture 24 along a first portion irrigation fluid path 68 to the instrument port 12. A second portion of the irrigation fluid moves through the second aperture 26 along a second portion irrigation path 69 to the suction port 14.

Figure 5:
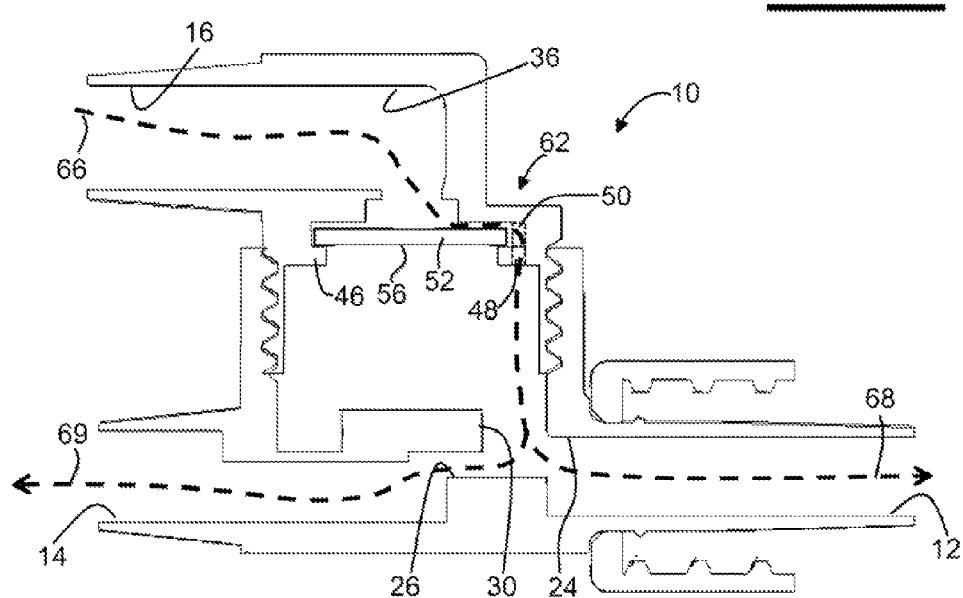
FIG. 5 illustrates a cross-sectional view of a multi-way valve of FIG. 1 cut along lines II-II in accordance with the teachings herein.

FIG. 5 illustrates a cross-sectional view of the multi-way valve 10 taken along line II-II of FIG. 1. Irrigation fluid supplied to the irrigation port 16 and into the secondary line 36 moves along the main irrigation fluid path 66. Movement the irrigation fluid causes the occluder, disk and/or membrane 52 to move, translate, and/or deflect, from the first occluder position 60 to the second occluder position 62 so that at least a portion of the downstream face 56 engages at least a portion of downstream retaining surface 46. The irrigation fluid moves along the main irrigation fluid path 66 around the occluder 52, through the wall passages 50 and the surface passages 48, and into the third aperture 30. A first portion of the irrigation fluid moves through the first aperture 24 along the first portion irrigation fluid path 68 to the instrument port 12, while a second portion of the irrigation fluid moves through the second aperture 26 along a second portion irrigation path 69 to the suction port 14.

Figure 6:
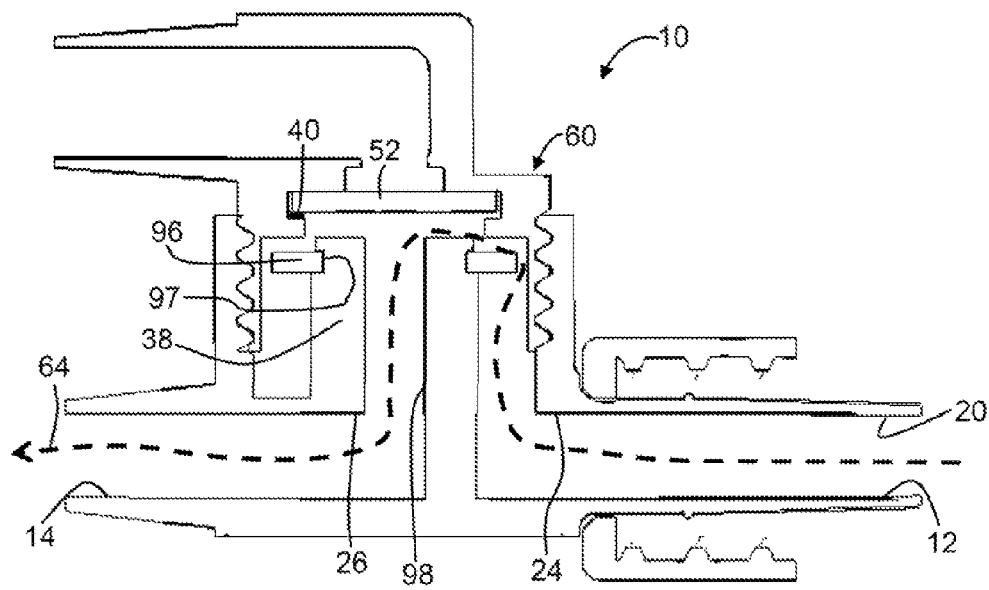
FIG. 6 illustrates a cross-sectional view of a multi-way valve of FIG. 1 cut along lines II-II in accordance with the teachings herein.

FIG. 6 illustrates a cross-sectional view of the multi-way valve 10 taken along line II-II of FIG. 1. A suction source 74 (FIG. 8) draws or communicates suction from the instrument port 12 to the suction port 14 via the primary line 20. With the occluder 52 in the first occluder position 60, the suction moves or communicates along the suction path 64. A biasing member 40 is configured to bias the upstream face 54 against the upstream sealing surface 44. The suction path 64 moves through the first aperture 24 and up and around a ring baffle 96 disposed around a groove 97 in the stalk 38. The suction path 64 is then directed into a passage 98 in the stalk 38 and through the second aperture 26 to the suction port 14

Figure 7:
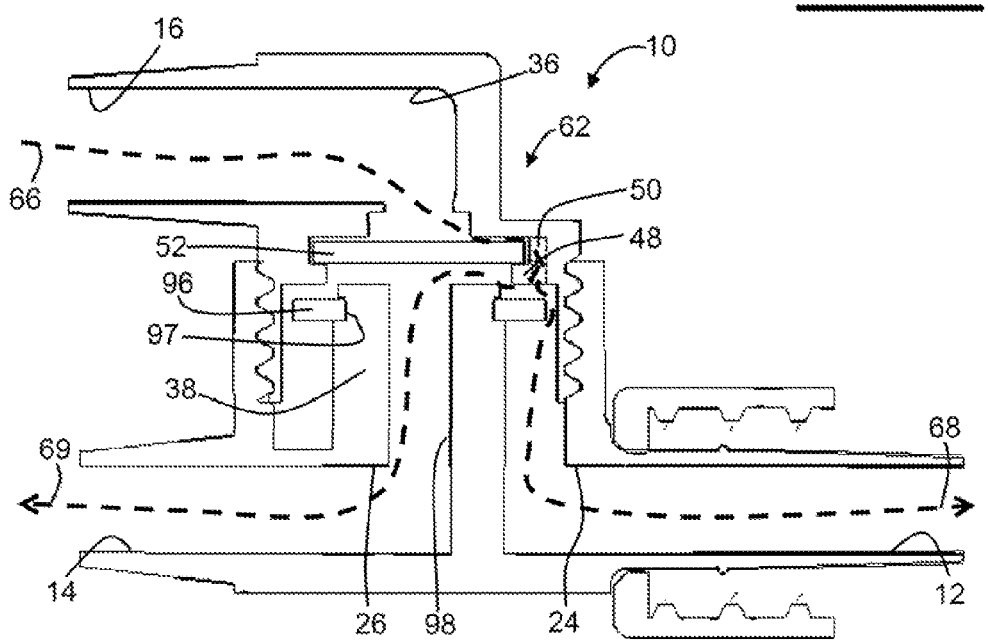
FIG. 7 illustrates a cross-sectional view of a multi-way valve of FIG. 1 cut along lines II-II in accordance with the teachings herein.

FIG. 7 illustrates a cross-sectional view of the multi-way valve 10 taken along line II-II of FIG. 1. An irrigation source 72 (See FIG. 8) supplies irrigation fluid to the secondary line 36 through the irrigation port 16 along the main irrigation fluid path 66. Movement the irrigation fluid moves the occluder 52 to the second occluder position 62. The irrigation fluid moves around the occluder 52 and through the wall passages 50 and the surface passages 48. A first portion of the irrigation fluid moves around a ring baffle 96 disposed around a groove 97 in the stalk 38 along a first portion irrigation fluid path 68, through the first aperture 24 to the instrument port 12. A second portion of the irrigation fluid moves through a passage 98 in the stalk 38 along a second portion irrigation path 69 and through the second aperture 26 to the suction port 14.

Figure 8:
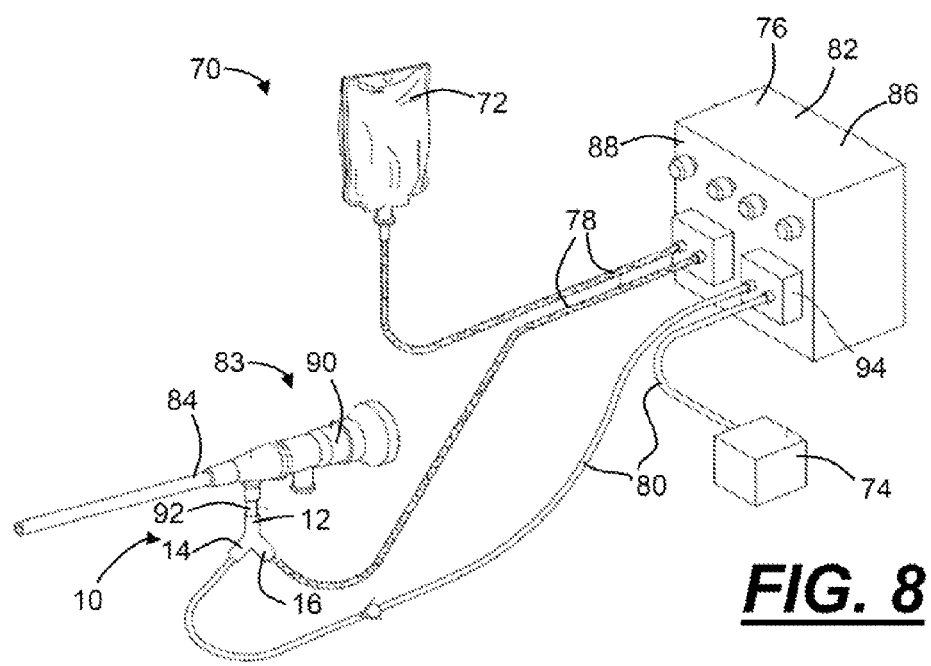
FIG. 8 illustrates a system for use with the endoscope, the endoscope sheath and the multi-way valve of the teachings herein in accordance with the teachings herein.

FIG. 8 illustrates an endoscope cleaning system 70. The endoscope cleaning system 70 includes an irrigation source 72 and a suction source 74 connected to a control module 76 via an irrigation line 78 and a suction line 80, respectively. The irrigation line 78 and the suction line 80 are connected to an irrigation port 16 and a suction port 14, respectively, on a multi-way valve 10. An instrument port 12 on the multi-way valve 10 connects the multi-way valve 10 to a valve adapter 92, which connects the multi-way valve 10 to a medical instrument or assembly 83, such as an endoscope sheath 84 for cleaning an endoscope 90. The control module 76 includes a pump 82 controlling a flow of irrigation fluid from the irrigation source 72 to the multi-way valve 10. A valve 94 controls suction between the suction source 74 and the multi-way valve 10. The control module 76 includes a power source 86 and a controller and/or microprocessor (not specifically illustrated) in communication with a user interface 88. The user interface 88 controls the control module 76.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A medical device comprising: a first port; a second port in fluid communication with the first port; a third port in selective fluid communication with both the first port and the second port; an upstream sealing surface; a plurality of downstream retaining surfaces; a surface passage defined between adjacent downstream retaining surfaces; a chamber wall extending between the upstream sealing surface and the downstream retaining surfaces; a plurality of wall passages that are notches defined in the chamber wall; a sealing membrane located between the upstream sealing surface and the downstream retaining surfaces, the sealing membrane is disposed between the third port and both the first port and the second port; and a resilient biasing member that is a spring that is located on at least one of the downstream retaining surfaces, the resilient biasing member is in contact with an edge portion of a downstream face of the sealing membrane, wherein during a condition of reduced or no-flow of fluid at the third port, the biasing member biases the sealing member into a first position so that an upstream face of the sealing membrane at least partially engages the upstream sealing surface preventing fluid communication between the third port and both the first port and the second port, wherein movement of the fluid supplied to the third port causes the biasing member to compress allowing the fluid to move the sealing membrane from the first position to a second position so that the upstream face of the sealing member disengages the upstream sealing surface and the downstream face of the sealing membrane at least partially engages the downstream retaining surfaces allowing fluid communication through at least some of the surface passages and at least some of the wall passages between the third port and the first port.

2. The medical device of claim 1, wherein a stalk contacts at least a portion of the downstream face of the sealing membrane when the sealing membrane is in both the first position and the second position, the sealing membrane is configured to move and at least partially deform about the stalk when the sealing membrane moves from the first position to the second position so that fluid can communicate between the third port and the first port, and wherein the movement of the fluid supplied to the medical device at the third port moves and at least partially deforms the sealing membrane about the stalk.

3. The medical device of claim 2, wherein the first port is an instrument port and the third port is an irrigation port, wherein the instrument port is configured to connect with a medical instrument, wherein the irrigation port is configured to connect with an irrigation source, the fluid supplied to the medical device is irrigation fluid supplied by the irrigation source.

4. The medical device of claim 3, wherein the second port is a suction port that is configured to connect with a suction source, wherein in the second position at least a first portion of the irrigation fluid communicates from the irrigation port directly to the instrument port and at least a second portion of the irrigation fluid communicates from the irrigation port directly to the suction port, and wherein the first portion of the irrigation fluid includes a volume of fluid that is larger than the second portion of the irrigation fluid.

5. The medical device of claim 4, wherein when the sealing membrane is in the first position the suction source is configured to communicate suction from the instrument port to the suction port.

6. The medical device of claim 4, wherein a passageway extends between the instrument port and the suction port, the passageway also extends between the irrigation port and the suction port, wherein the passageway provides fluid communication between the instrument port and the suction port when the sealing membrane is in the first position, and wherein the passageway provides fluid communication between the irrigation port and the suction port when the sealing membrane is in the second position.

7. A medical device comprising:

a first port that is an instrument port, the first port is configured to connect with a medical instrument;

a second port in fluid communication with the first port, the second port is a suction port that is configured to connect with a suction source;

a third port in selective fluid communication with both the first port and the second port, the third port is an irrigation port that is configured to connect with an irrigation source;

an upstream sealing surface;

a plurality of downstream retaining surfaces;

a surface passage defined between adjacent downstream retaining surfaces;

a chamber wall extending between the upstream sealing surface and the downstream retaining surface;

a plurality of wall passages that are notches defined in the chamber wall;

a sealing membrane located between the upstream sealing surface and the downstream retaining surfaces, the sealing membrane is configured to be moved between a first position and a second position;

a stalk that contacts at least a center portion of a downstream face of the sealing membrane when the sealing membrane is in both the first position and the second position; and a biasing member that is a spring, the spring is located on at least one of the downstream retaining surfaces, the spring is in contact with an edge portion of the downstream face of the sealing membrane, wherein during a condition of reduced or no-flow of fluid at the irrigation port, the spring biases the sealing member into the first position so that the upstream face of the sealing membrane at least partially engages the upstream sealing surface preventing irrigation fluid communication between the third port and both the first port and the second port, wherein movement of the fluid supplied to the irrigation port causes the spring to compress allowing the fluid to move the sealing membrane from the first position to the second position so that the upstream face of the sealing member disengages the upstream sealing surface and a downstream face of the sealing membrane at least partially engages the downstream retaining surfaces allowing irrigation fluid communication through at least some of the surface passages and at least some of the wall passages between the third port and the first port, wherein when the sealing membrane is in the second position, at least a first portion of the irrigation fluid communicates from the irrigation port directly to the instrument port and at least a second portion of the irrigation fluid communicates from the irrigation port directly to the suction port, wherein movement of the irrigation fluid supplied to the medical device at the third port moves the sealing membrane from the first position to the second position and compresses the spring, and the sealing membrane at least partially deforms about the stalk when moving from the first position to the second position.

* * * * *